(12) United States Patent
Jung et al.

(10) Patent No.: US 11,622,984 B2
(45) Date of Patent: Apr. 11, 2023

(54) COMPOSITION COMPRISING ASTER SPHATHULIFOLIUS MAXIM EXTRACT FOR PREVENTING, IMPROVING, OR TREATING MUSCULAR DISEASES OR FOR IMPROVING MUSCULAR FUNCTIONS

(71) Applicants: NEWTREE CO., LTD., Seongnam-Si (KR); Woo Chang Jung, Seoul (KR)

(72) Inventors: Woo Chang Jung, Seoul (KR); Do Un Kim, Seongnam-Si (KR); Hee Chul Chung, Seongnam-Si (KR)

(73) Assignee: NEWTREE CO., LTD., Seongnam-si (KR)

( * ) Notice: Subject to any disclaimer, the term of this patent is extended or adjusted under 35 U.S.C. 154(b) by 170 days.

(21) Appl. No.: 17/059,998

(22) PCT Filed: May 20, 2019

(86) PCT No.: PCT/KR2019/006030
§ 371 (c)(1),
(2) Date: Nov. 30, 2020

(87) PCT Pub. No.: WO2019/231150
PCT Pub. Date: Dec. 5, 2019

(65) Prior Publication Data
US 2021/0228666 A1    Jul. 29, 2021

(30) Foreign Application Priority Data
May 28, 2018    (KR) .................. 10-2018-0060713

(51) Int. Cl.
| | | |
|---|---|---|
| *A61K 36/28* | (2006.01) | |
| *A23K 10/30* | (2016.01) | |
| *A23L 33/105* | (2016.01) | |
| *A23L 33/00* | (2016.01) | |
| *A61K 8/9789* | (2017.01) | |
| *A61P 21/06* | (2006.01) | |
| *A61Q 19/00* | (2006.01) | |

(52) U.S. Cl.
CPC .............. *A61K 36/28* (2013.01); *A23K 10/30* (2016.05); *A23L 33/105* (2016.08); *A23L 33/40* (2016.08); *A61K 8/9789* (2017.08); *A61P 21/06* (2018.01); *A61Q 19/00* (2013.01); *A23V 2002/00* (2013.01); *A61K 2236/331* (2013.01); *A61K 2236/35* (2013.01); *A61K 2236/37* (2013.01)

(58) Field of Classification Search
None
See application file for complete search history.

(56) References Cited

FOREIGN PATENT DOCUMENTS

| | | | |
|---|---|---|---|
| KR | 10-2008-0004466 A | | 1/2008 |
| KR | 10-2015-0115973 A | | 10/2015 |
| KR | 20150115973 A | * | 10/2015 |
| KR | 10-2015-0130006 A | | 11/2015 |
| KR | 10-2016-0138926 A | | 12/2016 |
| KR | 10-2016-0138927 A | | 12/2016 |
| KR | 10-2018-0048416 A | | 5/2018 |

OTHER PUBLICATIONS

Cho et al. (2016) Nutrition Research 36: 671-678. (Year: 2016).*
Raskin et al. (2004) Current Pharmaceutical Design 10: 3419-3429. (Year: 2004).*
Revilla et al. (1998) J. Agric. Food Chem. 46: 4592-4597. (Year: 1998).*
Jang et al., "Anti-obesity and Hypolipidemic effects of Aster spathulifolius Maxim. in high fat diet induced obese rats", Forum 2004: Pharmaceutical Health Science Environmental Toxicology, Department of Hygienic Chemistry, College of Pharmacy, Hyung Hee University, Seoul, Korea, 2004.
Yin et al., "In vitro Efficacy Evaluation for Prevention of Diabetes and Diabetic Complications Using Aster sphathulifolius", Food Sci. Biotechnol., 2015, 24(1): 301-306.

* cited by examiner

*Primary Examiner* — Russell G Fiebig
(74) *Attorney, Agent, or Firm* — James S. Keddie; Bozicevic, Field & Francis LLP (57) ABSTRACT

The present invention relates to a composition comprising *Aster sphathulifolius* Maxim extract for preventing, improving, or treating muscular diseases and for improving muscular functions. The *Aster sphathulifolius* Maxim extract according to the present invention exhibits effects of inhibiting the expression of muscle protein breakdown-related factors and increasing the expression of muscle protein synthesis-related factors, as well as alleviating the reduction of muscle tissue weight and cross-sectional area of muscle fibers, and thus can be useful for preventing, improving, or treating muscular diseases and improving muscular functions.

4 Claims, 5 Drawing Sheets

COMPOSITION COMPRISING ASTER SPHATHULIFOLIUS MAXIM EXTRACT FOR PREVENTING, IMPROVING, OR TREATING MUSCULAR DISEASES OR FOR IMPROVING MUSCULAR FUNCTIONS

CROSS-REFERENCE TO RELATED APPLICATIONS

This application is a § 371 national phase of International Application No. PCT/KR2019/006030, filed on May 20, 2019, which claims the benefit of Korean Patent Application No. 10-2018-0060713, filed on May 28, 2018, which applications are incorporated by reference herein.

The present invention relates to a composition for preventing, improving or treating muscular diseases, or improving muscular functions, comprising an *Aster spathulifolius* extract, and more particularly, to a pharmaceutical composition for preventing or treating muscular diseases, a food composition for preventing or improving muscular diseases, a composition for livestock feed for preventing or improving muscular diseases, a cosmetic composition for improving muscular functions, and a composition for livestock feed for improving muscular functions.

BACKGROUND ART

Skeletal muscle is an organ that occupies the largest part of the human body and accounts for 40% to 50% of the total body weight, and plays an important role in various metabolic functions in the body, including energy homeostasis and heat generation. The muscle size is regulated by intracellular signaling pathways that induce anabolism or catabolism occurring within the muscle.

On the other hand, muscle atrophy is caused by a continuous decrease in muscle mass, and is weakness and degeneration of the muscle. The muscle atrophy is induced by decreased activity, oxidative stress, and chronic inflammation, and weakens muscular functions and motor ability. The muscle atrophy occurs when protein degradation occurs more than protein synthesis.

A representative factor involved in muscular protein synthesis, mTOR, induces the muscular protein synthesis by activating two factors that initiate mRNA translation, 4E-binding protein (4EBP1) and phosphorylated 70-kDa ribosomal S6 kinase (p70S6K), to contribute to increased muscle mass. A representative factor involved in muscular protein synthesis includes atrogin-1 and MuRF-1 which are E3 ubiquitin ligase factors, and the expression thereof is greatly increased when the activity thereof is decreased. When the expression levels thereof are increased, the protein degradation in muscle is promoted and the muscle mass decreases. Therefore, the amount of muscular proteins is increased by promoting the activity of mTOR and inhibiting the expression of atrogin-1 and MuRF-1 to increase the muscle mass.

Currently, as a therapy for muscle atrophy, increased mitochondrial production, muscular protein degradation inhibitors, and anti-inflammatory agents have been proposed, but there are no clear therapeutic drugs.

*Aster spathulifolius* is a plant belonging to the Asteraceae family. It has been reported that the *Aster spathulifolius* has the activity of anti-obesity (Nutr Res, 36(7):671-8, 2016), anti-influenza virus (J Microbiol Biotechnol, 23(1):125-30, 2013), and anti-cancer (J Nat Prod, 68(10):1471-4, 2005).

However, prior to the present invention, an effect of preventing and treating muscular diseases or improving muscle functions of the *Aster spathulifolius* extract has not been known.

DETAILED DESCRIPTION OF THE INVENTION

Technical Problem

Therefore, the present inventors have searched for a natural substance that had excellent muscular function regulation activity and may be safely applied, and as a result, found that an *Aster spathulifolius* extract had an effect on the expression of factors involved in muscular protein synthesis or degradation, and had an effect of alleviating the reduction in a muscle tissue weight and a cross-sectional area of muscle fibers due to muscle atrophy, and then completed the present invention.

Accordingly, an object of the present invention is to provide a pharmaceutical composition for preventing or treating muscular diseases comprising an *Aster spathulifolius* extract as an active ingredient.

Further, an object of the present invention is to provide a pharmaceutical composition for preventing or treating muscular diseases consisting of an *Aster spathulifolius* extract as an active ingredient.

Further, an object of the present invention is to provide a pharmaceutical composition for preventing or treating muscular diseases consisting essentially of an *Aster spathulifolius* extract as an active ingredient.

Another object of the present invention is to provide a food composition for preventing or improving muscular diseases comprising an *Aster spathulifolius* extract as an active ingredient.

Further, an object of the present invention is to provide a food composition for preventing or improving muscular diseases consisting of an *Aster spathulifolius* extract as an active ingredient.

Further, another object of the present invention is to provide a food composition for preventing or improving muscular diseases consisting essentially of an *Aster spathulifolius* extract as an active ingredient.

Yet another object of the present invention is to provide a cosmetic composition for improving muscular functions comprising an *Aster spathulifolius* extract as an active ingredient.

Further, yet another object of the present invention is to provide a cosmetic composition for improving muscular functions consisting of an *Aster spathulifolius* extract as an active ingredient.

Further, yet another object of the present invention is to provide a cosmetic composition for improving muscular functions consisting essentially of an *Aster spathulifolius* extract as an active ingredient.

Another object of the present invention is to provide a composition for livestock feed for preventing or improving muscular diseases comprising an *Aster spathulifolius* extract as an active ingredient.

Further, another object of the present invention is to provide a composition for livestock feed for preventing or improving muscular diseases consisting of an *Aster spathulifolius* extract as an active ingredient.

Further, another object of the present invention is to provide a composition for livestock feed for preventing or improving muscular diseases consisting essentially of an *Aster spathulifolius* extract as an active ingredient.

Another object of the present invention is to provide a composition for livestock feed for improving muscular functions comprising an *Aster spathulifolius* extract as an active ingredient.

Further, another object of the present invention is to provide a composition for livestock feed for improving muscular functions consisting of an *Aster spathulifolius* extract as an active ingredient.

Further, another object of the present invention is to provide a composition for livestock feed for improving muscular functions consisting essentially of an *Aster spathulifolius* extract as an active ingredient.

Another object of the present invention is to provide use of an *Aster spathulifolius* extract for preparing an agent for preventing or treating muscular diseases.

Another object of the present invention is to provide a method for treating muscular diseases in a subject in need thereof, the method comprising administering an effective amount of a composition comprising an *Aster spathulifolius* extract as an active ingredient to the subject in need thereof.

Another object of the present invention is to provide use of an *Aster spathulifolius* extract for preparing an agent for improving muscular functions.

Another object of the present invention is to provide a method for improving muscular functions in a subject in need thereof, the method comprising administering an effective dose of a composition comprising an *Aster spathulifolius* extract as an active ingredient to the subject in need thereof.

Technical Solution

In order to achieve the objects, the present invention provides a pharmaceutical composition for preventing or treating muscular diseases comprising an *Aster spathulifolius* extract as an active ingredient.

Further, the present invention provides a pharmaceutical composition for preventing or treating muscular diseases consisting of an *Aster spathulifolius* extract as an active ingredient.

Further, the present invention provides a pharmaceutical composition for preventing or treating muscular diseases consisting essentially of an *Aster spathulifolius* extract as an active ingredient.

In order to achieve another object of the present invention, the present invention provides a food composition for preventing or improving muscular diseases comprising an *Aster spathulifolius* extract as an active ingredient.

Further, the present invention provides a food composition for preventing or improving muscular diseases consisting of an *Aster spathulifolius* extract as an active ingredient.

Further, the present invention provides a food composition for preventing or improving muscular diseases consisting essentially of an *Aster spathulifolius* extract as an active ingredient.

In order to achieve yet another object of the present invention, the present invention provides a cosmetic composition for improving muscular functions comprising an *Aster spathulifolius* extract as an active ingredient.

Further, the present invention provides a cosmetic composition for improving muscular functions consisting of an *Aster spathulifolius* extract as an active ingredient.

Further, the present invention provides a cosmetic composition for improving muscular functions consisting essentially of an *Aster spathulifolius* extract as an active ingredient.

In order to achieve yet another object of the present invention, the present invention provides a composition for livestock feed for preventing or improving muscular diseases comprising an *Aster spathulifolius* extract as an active ingredient.

Further, the present invention provides a composition for livestock feed for preventing or improving muscular diseases consisting of an *Aster spathulifolius* extract as an active ingredient.

Further, the present invention provides a composition for livestock feed for preventing or improving muscular diseases consisting essentially of an *Aster spathulifolius* extract as an active ingredient.

In order to achieve yet another object of the present invention, the present invention provides a composition for livestock feed for improving muscular functions comprising an *Aster spathulifolius* extract as an active ingredient.

Further, the present invention provides a composition for livestock feed for improving muscular functions consisting of an *Aster spathulifolius* extract as an active ingredient.

Further, the present invention provides a composition for livestock feed for improving muscular functions consisting essentially of an *Aster spathulifolius* extract as an active ingredient.

In order to achieve yet another object of the present invention, the present invention provides use of an *Aster spathulifolius* extract for preparing an agent for preventing or treating muscular diseases.

In order to achieve yet another object of the present invention, the present invention provides a method for treating muscular diseases in a subject in need thereof, the method comprising administering an effective dose of a composition comprising an *Aster spathulifolius* extract as an active ingredient to the subject in need thereof.

In order to achieve yet another object of the present invention, the present invention provides use of an *Aster spathulifolius* extract for preparing an agent for improving muscular functions.

In order to achieve yet another object of the present invention, the present invention provides a method for improving muscular functions in a subject in need thereof, the method comprising administering an effective amount of a composition comprising an *Aster spathulifolius* extract as an active ingredient to the subject in need thereof.

Hereinafter, the present invention will be described in more detail.

The present invention provides a pharmaceutical composition for preventing or treating muscular diseases comprising an *Aster spathulifolius* extract as an active ingredient.

The pharmaceutical composition of the present invention may be a composition comprising an *Aster spathulifolius* extract as an active ingredient, a composition consisting of an *Aster spathulifolius* extract as an active ingredient, or a composition consisting essentially of an *Aster spathulifolius* extract as an active ingredient.

The term 'comprising' herein is used in the same meaning as 'including' or 'characterized by', and does not exclude additional ingredients or steps of the method which are not mentioned in the composition or the method according to the present invention. The term 'consisting of' means excluding additional elements, steps or ingredients, etc., unless otherwise described. The term 'consisting essentially of' means including substances or steps which do not substantially affect basic properties thereof in addition to the described substances or steps within the range of the composition or the method.

'*Aster spathulifolius* Maximowicz' of the present invention is a plant of the Asteraceae family, and is a perennial herb growing on the beach. In particular, the *Aster spathulifolius* grows on a sunny rock wall or in an inclined place, is 30 to 60 cm tall, has many villi on both sides, and has leaves which are unfolded like a bunch when viewed from the top and have little gap between leaves. The upper leaves remain in a semi-evergreen state that does not wither even in winter. Flowers are light purple, hang one by one at the end of the branches, and have the diameter of 3.5 to 4 cm. Currently, it is reported that the *Aster spathulifolius* has anti-obesity, anti-influenza virus, and anti-cancer activity.

In this specification, the 'muscle' collectively refers to tendons, muscles, and chords, and the 'muscular function' refers to the ability to exert power by contraction of muscles, and includes muscular strength which is the ability of the muscles to exert maximum contraction to overcome resistance, muscular endurance which is the ability to exhibit how long or how many times muscles can repeat contraction and relaxation at a given weight, and quickness which is the ability to exert strong power in a short time. These muscle functions are controlled by the liver and are proportional to muscle mass. The term 'improving muscle functions' means improving muscle functions in a more positive direction.

The term 'muscular diseases' of the present invention means diseases caused by muscle wasting or degeneration. Examples of the diseases may include sarcopenia, atony, muscular atrophy, muscular dystrophy, muscle degeneration, myotonia, muscular dystrophy, amyotrophic lateral sclerosis, myasthenia and cachexia. The muscle wasting is characterized by gradual loss of muscle mass, weakness and degeneration of muscles, especially skeletal or voluntary and cardiac muscles. The muscle wasting and degeneration occur due to genetic factors, acquired factors, and aging. An *Aster spathulifolius* extract of the present invention has an effect of inhibiting the expression of muscle degradation factors, increasing the expression of muscle synthesis factors, and alleviating the reduction in muscle cross-sectional area, and the type of muscle is not limited. The muscle mass may be increased through physical exercise and endurance improvement in addition to the administration of the composition according to the present invention, and the muscle mass is increased by administering a substance having a muscle increasing effect to the body to improve or treat the muscle diseases.

The pharmaceutical composition for preventing or treating muscle diseases of the present invention may contain one or more active ingredients exhibiting a function similar to that of the *Aster spathulifolius* extract according to the present invention. When the additional ingredients are included, the effect of treating the muscular diseases may be further enhanced by the composition according to the present invention. When the ingredients are added, skin safety, ease of formulation, and stability of active ingredients may be considered according to combination use.

The *Aster spathulifolius* extract of the present invention may include a pre-treatment process such as a drying process for raw materials in order to increase the extraction efficiency when the extract is prepared.

The *Aster spathulifolius* extract of the present invention may be extracted by a known natural product extraction method. Preferably, the *Aster spathulifolius* extract may be extracted with one or more solvents selected from the group consisting of water, organic solvents having 1 to 6 carbon atoms, and subcritical or supercritical fluids. The organic solvent having 1 to 6 carbon atoms may be selected from the group consisting of alcohol having 1 to 6 carbon atoms, acetone, ether, benzene, chloroform, ethyl acetate, methylene chloride, hexane, cyclohexane, and petroleum ether, but is not limited thereto.

In addition, the *Aster spathulifolius* extract of the present invention may be obtained by extracting and purifying *Aster spathulifolius* using purified water, ethanol, and subcritical water, or supercritical carbon dioxide which are suitable for food processing, or may be obtained by separating and purifying from oil obtained by directly pressing *Aster spathulifolius*. For example, the extract may be obtained by extracting *Aster spathulifolius* under ultra-high pressure conditions of 100 Mpa or more. Preferably, the condition may be an ultra-high pressure condition of 100 MPa to 1000 MPa, but is not limited thereto.

According to an embodiment of the present invention, after the ground part of *Aster spathulifolius* is powdered, a solvent obtained by mixing water and ethyl alcohol is added thereto, and then an extract extracted by reflux cooling method is used.

The extract of the present invention may be filtered and/or concentrated to be used as a liquid, and may be solidified and used through a general drying process such as spray drying or freeze drying. In the drying process, dextrin or the like may be mixed and dried before spray drying or freeze drying.

The pharmaceutical composition for preventing and treating muscle diseases of the present invention may further comprise a pharmaceutically acceptable carrier.

The pharmaceutically acceptable carrier may further include, for example, a carrier for oral administration or a carrier for parenteral administration. The carrier for oral administration may include lactose, starch, cellulose derivatives, magnesium stearate, stearic acid, and the like. In addition, the carrier for parenteral administration may include water, suitable oil, saline, aqueous glucose, glycol, and the like. In addition, a stabilizer and a preservative may be further included. A suitable stabilizer includes antioxidants such as sodium hydrogen sulfite, sodium sulfite or ascorbic acid. A suitable preservative includes benzalkonium chloride, methyl- or propyl-paraben and chlorobutanol. Other pharmaceutically acceptable carriers may refer to those known in the art.

The pharmaceutical composition of the present invention may be administered to mammals including humans by any method. For example, the pharmaceutical composition may be administered orally or parenterally, and the parenteral administration method is not limited thereto, but may include intravenous, intramuscular, intraarterial, intramedullary, intrathecal, intracardiac, transdermal, subcutaneous, intraperitoneal, Intranasal, intestinal, topical, sublingual or rectal administration.

The pharmaceutical composition of the present invention may be formulated as a preparation for oral administration or parenteral administration according to the route of administration as described above. The formulation may be prepared by using one or more buffers (e.g., saline or PBS), antioxidants, bacteriostatic agents, chelating agents (e.g., EDTA or glutathione), fillers, extenders, binders, adjuvants (e.g., aluminum hydroxide), suspending agents, thickening agents, wetting agents, disintegrants or surfactants, and diluents or excipients.

Solid preparations for oral administration include tablets, pills, powders, granules, liquids, gels, syrups, slurries, suspensions or capsules. These solid preparations may be prepared by mixing at least one excipient, for example, starch (including corn starch, wheat starch, rice starch, potato starch, etc.), calcium carbonate, sucrose, lactose, dextrose, sorbitol, mannitol, xylitol, erythritol maltitol, cellulose, methyl cellulose, sodium carboxymethyl cellulose and hydroxypropyl methyl cellulose or gelatin with the pharmaceutical composition of the present invention. For example, tablets or sugar-coated tablets may be obtained by mixing an active ingredient with a solid excipient, pulverizing the mixture, adding a suitable auxiliary, and then processing the mixture into a granule mixture.

Lubricants such as magnesium stearate and talc may be used in addition to simple excipients. Liquid preparations for oral administration may correspond to suspensions, oral liquids, emulsions, syrups, or the like, and may include various excipients, for example, a wetting agent, a sweetener, an aromatic agent, a preserving agent, and the like in addition to water or liquid paraffin which is a commonly used simple diluent.

In addition, in some cases, cross-linked polyvinylpyrrolidone, agar, alginic acid or sodium alginate may be added as a disintegrant, and an anti-coagulant, a lubricant, a wetting agent, a fragrance, an emulsifier, a preservative, and the like may be additionally included.

When administered parenterally, the pharmaceutical composition of the present invention may be formulated according to a method known in the art in the form of injections, transdermal agents, and nasal inhalers together with suitable parenteral carriers. The injections need to be sterilized and protected from contamination of microorganisms such as bacteria and fungi. Examples of suitable carriers for injections may include, but are not limited to, solvents or dispersion media containing water, ethanol, polyols (e.g., glycerol, propylene glycol, and liquid polyethylene glycols), mixtures thereof and/or vegetable oils. More preferably, as the suitable carriers, a Hanks' solution, a Ringer's solution, a phosphate buffered saline (PBS) containing triethanol amine or sterile water for injection, an isotonic solution such as 10% ethanol, 40% propylene glycol and 5% dextrose, and the like may be used. In order to protect the injection from microbial contamination, various antibacterial and antifungal agents such as paraben, chlorobutanol, phenol, sorbic acid, thimerosal, and the like may be further included. In addition, most of the injections may further include an isotonic agent, such as sugar or sodium chloride.

The transdermal agents are included in the form of ointments, creams, lotions, gels, external liquids, pastas, liniments, and aerosols. Hereinabove, the 'transdermal administration' means that an effective dose of the active ingredient contained in the pharmaceutical composition is delivered into the skin by topically applying the pharmaceutical composition to the skin.

In the case of the inhalers, the *Aster spathulifolius* extract of the present invention may be conveniently delivered in the form of an aerosol spray from a pressurized pack or a nebulizer by using a suitable propellant, for example dichlorofluoromethane, trichlorofluoromethane, dichlorotetrafluoroethane, and carbon dioxide, or other suitable gas. In the case of a pressurized aerosol, a dosage unit may be determined by providing a valve that delivers a metered amount. For example, gelatin capsules and cartridges used in an inhaler or insufflator may be formulated to contain a powder mixture of a compound and a suitable powder base such as lactose or starch. Formulations for parenteral administration are generally known in all pharmaceutical chemistries.

The pharmaceutical composition for preventing and treating muscle diseases of the present invention may provide a desirable effect of preventing and treating muscle diseases when the *Aster spathulifolius* extract is contained in an effective dose. In this specification, the term 'effective dose' refers to an amount that exhibits a higher response than a negative control group, and preferably an amount sufficient to alleviate muscle atrophy or improve muscle functions. The *Aster spathulifolius* extract may be contained in an amount of 0.01 to 99.99% in the pharmaceutical composition of the present invention, and the remaining amount may be occupied by the pharmaceutically acceptable carrier. The effective dose of the *Aster spathulifolius* extract contained in the pharmaceutical composition of the present invention will vary depending on the form in which the composition is commercialized.

In the present specification, 'treatment' refers to a clinical procedure to change a natural process of a subject or cells to be treated, and may be performed to prevent clinical pathology. Preferable effects of the treatment include inhibition of the occurrence or recurrence of diseases, alleviation of symptoms, reduction in any direct or indirect pathological consequences of diseases, reduction in the rate of disease progression, improvement, amelioration, and alleviation of disease conditions, or improved prognosis, etc. Also, the term 'prevention' refers to all actions that inhibit the occurrence of diseases or delay the progression of diseases. The total effective dose of the pharmaceutical composition of the present invention may be administered to a patient in a single dose, or may be administered to the subject in a multiple dose for a long period of time according to a fractionated treatment protocol. In the pharmaceutical composition of the present invention, the content of the active ingredient may vary depending on the severity of disease. In the parenteral administration, the pharmaceutical composition may be administered preferably in an amount of 0.01 to 50 mg, more preferably 0.1 to 30 mg per 1 kg of body weight per day based on the *Aster spathulifolius* extract. In addition, in the oral administration, the pharmaceutical composition may be administered one or several times preferably in an amount of 0.01 to 100 mg, more preferably 0.1 to 10 mg per 1 kg of body weight per day based on the *Aster spathulifolius* extract. However, the effective dose of the *Aster spathulifolius* extract to the patient is determined by considering various factors including the age, body weight, health conditions, and gender of the patient, the severity of disease, diet, and excretion rate, in addition to an administration route and the number of treatment times of the pharmaceutical composition. Accordingly, considering such an aspect, those skilled in the art may determine an effective dose of the *Aster spathulifolius* extract suitable for a specific use for preventing and treating muscular diseases. So long as the pharmaceutical composition according to the present invention exhibits the effects of the present invention, formulations thereof, routes of administration, and methods of administration are not particularly limited.

The pharmaceutical composition for preventing or treating muscle diseases of the present invention may be used alone or in combination with surgery, radiation therapy, hormonal therapy, chemotherapy, or methods using a biological response modifier.

The pharmaceutical composition for preventing or treating muscle diseases of the present invention may also be provided in the form of an external preparation containing the *Aster spathulifolius* extract as an active ingredient.

When the pharmaceutical composition for preventing or treating muscle diseases of the present invention is used as an external skin preparation, the pharmaceutical composition may further contain adjuvants commonly used in the field of dermatology such as any other ingredients commonly used in external skin preparations, such as fatty substances, organic solvents, solubilizers, thickening and gelling agents, emollients, antioxidants, suspending agents, stabilizers, foaming agents, fragrances, surfactants, water, ionic emulsifiers, nonionic emulsifiers, fillers, sequestering agents, chelating agents, preservatives, vitamins, blockers, wetting agents, essential oils, dyes, pigments, hydrophilic activators, lipophilic activators or lipid vesicles. In addition, the ingredients may be introduced in an amount generally used in the field of dermatology.

When the pharmaceutical composition for preventing or treating muscle diseases of the present invention is provided as an external skin preparation, the external skin preparation may be a formulation such as an ointment, a patch, gel, cream, or spray, but is not limited thereto.

Further, the present invention provides a food composition for preventing or improving muscular diseases comprising an *Aster spathulifolius* extract as an active ingredient.

The food composition according to the present invention may be used to prevent or improve muscle diseases caused by muscle wasting or degeneration. The muscle wasting and degeneration occur due to genetic factors, acquired factors, aging, etc., and the muscle wasting is characterized by a gradual loss of muscle mass, weakness and degeneration of muscles, especially skeletal or voluntary muscle and cardiac muscle. Examples of the diseases related thereto may include sarcopenia, atony, muscular atrophy, muscular dystrophy, muscle degeneration, myotonia, muscular dystrophy, amyotrophic lateral sclerosis, myasthenia and cachexia. The composition of the present invention has a muscle reduction and relaxation effect, and the type of muscle is not limited.

The food composition of the present invention includes all forms such as functional food, nutritional supplement, health food, food additives, etc., and is taken for animals including humans or livestock. The type of food composition may be prepared in various forms according to a general method known in the art.

The type of food composition may be prepared in various forms according to a general method known in the art. General foods are not limited thereto, but may be prepared by adding the *Aster spathulifolius* extract to beverages (including alcoholic beverages), fruits and processed foods thereof (e.g., canned fruit, bottled food, jam, marmalade, etc.), fish, meat and processed foods thereof (e.g. ham, sausage, corned beef, etc.), bread and noodles (e.g. udon, buckwheat noodles, ramen, spaghetti, macaroni, etc.), fruit juice, various drinks, cookies, sweets, dairy products (e.g. butter, cheese, etc.), edible vegetable oil, margarine, vegetable protein, retort food, frozen food, various seasonings (e.g., soybean paste, soy sauce, sauce, etc.), etc. In addition, the nutritional supplement is not limited thereto, but may be prepared by adding the *Aster spathulifolius* extract to capsules, tablets, pills, etc. In addition, the health functional food is not limited thereto, but for example, may be taken by liquefying, granulating, encapsulating, and powdering so as to be drunken (health beverages) by preparing the *Aster spathulifolius* extract itself in the form of tea, juice, and drinks. In addition, in order to use the *Aster spathulifolius* extract in the form of food additives, the *Aster spathulifolius* extract may be prepared and used in the form of powder or concentrate. In addition, the *Aster spathulifolius* extract may be mixed with known active ingredients to have an effect on improving muscle diseases and muscle functions to be prepared in the form of a composition.

When the food composition of the present invention is used as a health drink composition, the health drink composition may contain various flavoring agents or natural carbohydrates as an additional ingredient, like a general drink. The natural carbohydrates described above include monosaccharides such as glucose and fructose; disaccharides such as maltose and sucrose; polysaccharides such as dextrin and cyclodextrin; and sugar alcohols such as xylitol, sorbitol, and erythritol. As the sweetening agent, natural sweetening agents such as thaumatin and a *Stevia* extract; synthetic sweetening agents such as saccharin and aspartame, and the like may be used. A ratio of the natural carbohydrate may be generally about 0.01 to 0.04 g, preferably about 0.02 to 0.03 g per 100 mL of the composition of the present invention.

When the *Aster spathulifolius* extract according to the present invention is contained as an active ingredient in the food composition for preventing or improving muscle diseases, the amount thereof is not particularly limited to an effective dose to achieve an effect of improving muscle diseases and muscle functions, but is preferably 0.01 to 100 wt % based on the total weight of the total composition. The food composition of the present invention may be prepared by mixing the *Aster spathulifolius* extract with other active ingredients known to have an effect on improving muscle diseases and muscle functions.

In addition, when the food composition of the present invention is used as health food, the food composition may contain various nutrients, vitamins, electrolytes, flavoring agents, coloring agents, pectic acid and salts thereof, alginic acid and salts thereof, organic acid, protective colloidal thickeners, pH adjusting agents, stabilizers, preservatives, glycerin, alcohol, carbonic acid agents, or the like. In addition, the health food of the present invention may contain pulp for preparing natural fruit juice, fruit juice beverage or vegetable beverage. These ingredients may be used independently or in combination. Although the ratio of these additives is not very important, generally, the ratio thereof is selected in a range of 0.01 to 0.1 parts by weight per 100 parts by weight of the composition of the present invention.

Further, the present invention provides a cosmetic composition for improving muscular functions comprising an *Aster spathulifolius* extract as an active ingredient.

The cosmetic composition of the present invention contains the *Aster spathulifolius* extract as an active ingredient, and may be prepared in the form of a basic cosmetic composition (lotion, cream, essence, face cleanser such as cleansing foam and cleansing water, packs, and body oils), a colored cosmetic composition (foundation, lipstick, mascara, and makeup base), a hair product composition (shampoo, conditioner, hair conditioner, and hair gel), soap, etc., in addition to dermatologically acceptable excipients.

The excipient is not limited thereto, but may include, for example, an emollient, a skin penetration enhancer, a colorant, a fragrance, an emulsifier, a thickener, and a solvent. In addition, flavors, pigments, disinfectants, antioxidants, preservatives and moisturizing agents may be additionally included, and thickeners, inorganic salts, synthetic polymer materials, and the like may be included for the purpose of improving physical properties. For example, in the case of preparing the face cleanser and the soap with the cosmetic composition of the present invention, the face cleanser and the soap may be easily prepared by adding the *Aster spathulifolius* extract to general face cleanser and soap base. In the case of preparing the cream, the cream may be prepared by adding the *Aster spathulifolius* extract or salts thereof to a general oil-in-water (O/W) type cream base. Synthetic or natural materials such as proteins, minerals, vitamins, etc. may be further added thereto for the purpose of improving physical properties, such as fragrances, chelating agents, pigments, antioxidants, preservatives, etc. The content of the *Aster spathulifolius* extract contained in the cosmetic composition of the present invention is not limited thereto, but is preferably 0.001 to 10 wt %, more preferably 0.01 to 5 wt % based on the total weight of the entire composition. When the content thereof is less than 0.001 wt %, a desired anti-aging or wrinkle improvement effect cannot be expected, and when the content thereof is more than 10 wt %, there may be difficulties in safety or formulation.

Further, the present invention provides a composition for livestock feed for preventing or improving muscular diseases comprising an *Aster spathulifolius* extract as an active ingredient.

Further, the present invention provides a composition for livestock feed for improving muscular functions comprising an *Aster spathulifolius* extract as an active ingredient.

The composition for livestock feed according to the present invention may be used to prevent or improve muscle diseases and improve muscular functions caused by muscle wasting or degeneration. The muscle wasting and degeneration occur due to genetic factors, acquired factors, aging, etc., and the muscle wasting is characterized by a gradual loss of muscle mass, weakness and degeneration of muscles, especially skeletal or voluntary muscle and cardiac muscle. Examples of the diseases related thereto may include sarcopenia, atony, muscular atrophy, muscular dystrophy, muscle degeneration, myotonia, muscular dystrophy, amyotrophic lateral sclerosis, myasthenia and cachexia. The composition of the present invention has a muscle reduction and relaxation effect, and the type of muscle is not limited. The livestock may be one selected from the group consisting of cows, pigs, chickens, ducks, goats, sheep and horses.

The feed composition may include a feed additive. The feed additive of the present invention corresponds to an auxiliary feed in the Control of Livestock and Fish Feed Act.

In the present invention, the term 'feed' may mean any natural or artificial diet, one-meal diet, or ingredients of one-meal diet to be eaten, ingested, and digested by animals or suitable thereto.

The type of feed is not particularly limited, and may use feeds commonly used in the art. Non-limiting examples of the feed may include vegetable feeds, such as grains, root fruits, food processing by-products, algae, fibers, pharmaceutical by-products, oils and fats, starches, meals or grain by-products; and animal feeds such as proteins, inorganic materials, oils and fats, minerals, oils and fats, single-cell proteins, animal planktons, foods, etc. These feeds may be used alone or in combination of two or more kinds.

In addition, the feed additive may additionally contain a carrier acceptable to a unit animal. In the present invention, the feed additive may be used as it is or added with known carriers, stabilizers, etc., and may be added with various nutrients such as vitamins, amino acids, and minerals, antioxidants, and other additives as necessary, and the shape thereof may be a suitable state such as powder, granules, pellets, suspensions, etc. In the case of supplying the feed additive of the present invention, the feed additive may be supplied to a unit animal alone or in combination with the feed.

The present invention provides use of an *Aster spathulifolius* extract for preparing an agent for preventing or treating muscular diseases.

The present invention provides a method for treating muscular diseases in a subject in need thereof, the method comprising administering an effective amount of a composition comprising an *Aster spathulifolius* extract as an active ingredient to the subject in need thereof.

The present invention provides use of an *Aster spathulifolius* extract for preparing an agent for improving muscular functions.

The present invention provides a method for improving muscular functions in a subject in need thereof, the method comprising administering an effective dose of a composition comprising an *Aster spathulifolius* extract as an active ingredient to a subject in need thereof.

The term 'effective amount' of the present invention means an amount which exhibits an effect of improving, treating, preventing, detecting, or diagnosing of muscular diseases or muscular functions, an effect of inhibiting or alleviating muscular diseases, or an effect of improving muscular functions when administered to the subject. The 'subject' may be animals, preferably, mammals, particularly animals including humans and may also be cells, tissues, and organs derived from animals. The subject may be a patient requiring the effects.

The 'treatment' of the present invention collectively refers to improving the reduction in muscle diseases or muscle functions, or symptoms of the reduction in muscle diseases or muscle functions. The treatment may include treating or substantially preventing the reduction in muscle diseases or muscle functions or improving conditions thereof, and include alleviating, treating, or preventing one symptom or most of symptoms including the reduction muscle diseases or muscle functions, but is not limited thereto.

Advantageous Effects

Accordingly, the present invention confirms that the *Aster spathulifolius* extract has effects of not only inhibiting the expression of muscle degradation-related factors and increasing the expression of muscle synthesis-related factors, but also alleviating the reduction of a muscle tissue weight and a cross-sectional area of muscle fibers. The *Aster spathulifolius* extract can be not only usefully used in the prevention, improvement or treatment of muscle diseases including muscular dystrophy, but also usefully used as a composition for improving muscle functions.

MODE FOR CARRYING OUT INVENTION

Hereinafter, a preferred embodiment will be proposed in order to help in understanding of the present invention. However, the following Examples are just provided to more easily understand the present invention and the contents of the present invention are not limited by Examples.

Example 1: Preparation of *Aster spathulifolius* Extract 1-1. Washing of Ground Part of *Aster spathulifolius* Using Water

*Aster spathulifolius* was collected from October to December in Jeju Island, Korea, and the ground part of *Aster spathulifolius* was dried at room temperature to be powdered, and then the powder passed through #4 sieve was used. 10 kg of powder of the ground part of *Aster spathulifolius* was added with 100 L of purified water, circulatory washed at room temperature, and dehydrated, and then the washing solution was discarded. The washing and dehydrating processes were repeated twice more, and at this time, the concentration of chlorine ions in the last washing solution was 10 ppm or less.

1-2. Preparation of Ground Part Extract of *Aster spathulifolius*

100 L of a mixed solvent of water and ethyl alcohol having a mixing ratio (v/v) of 1:10 was added to the washed ground part powder of *Aster spathulifolius*, and extracted by reflux cooling at about 85° C. to 100° C. for 2 to 5 hours, and the extract was filtered through filter paper. After the extraction process was repeated twice more, the filtrate was concentrated under reduced pressure and dried to obtain 503 g of a ground part extract of *Aster spathulifolius* in an oily state (AE-B).

Figure 1:
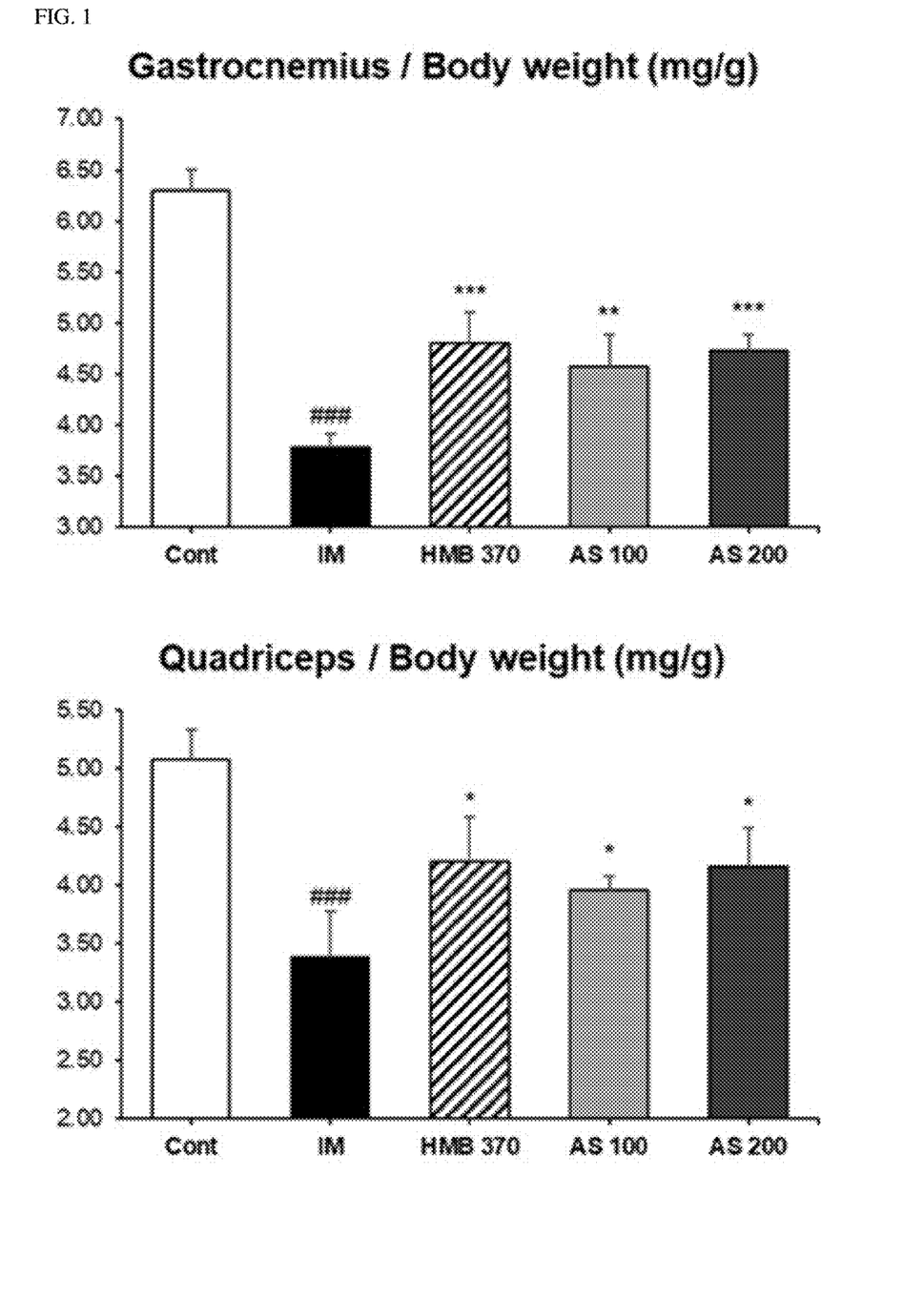
FIG. 1 illustrates a result of confirming an effect of alleviating a muscle weight loss of an *Aster spathulifolius* extract, as a result of dividing the weight of muscle tissue by the weight of each mouse according to the administration of the *Aster spathulifolius* extract in a muscle atrophy mouse model.

Example 2: Establishment of Muscle Atrophy-Induced Mouse Model and Measurement of Muscle Tissue Weight An animal experiment was conducted to confirm whether an *Aster spathulifolius* extract improved muscle atrophy in a muscle atrophy mouse model. Five-week-old male C57BL/6 mice were adapted to an animal laboratory environment for one week, and then divided into five groups according to an experimental condition, and immobilization of the legs to induce muscle atrophy and oral administration of samples were performed for two weeks. Specifically, experimental groups were divided into an untreated control group (normal group, Cont), a muscle atrophy induced group (induction group, IM), a positive control group (HMB administered group, HMB 370) induced with muscle atrophy and administered with beta-hydroxy beta-methylbutyrate (HMB) (370 mg/kg), a group (*Aster spathulifolius* low-dose administered group, AS 100) induced with muscle atrophy and administered with a low dose (100 mg/kg) of *Aster spathulifolius* extract, and a group (*Aster spathulifolius* high-dose administered group, AS 200) induced with muscle atrophy and administered with a high dose (200 mg/kg) of *Aster spathulifolius* extract. Immobilization of the legs was performed by applying a fixing tool manufactured by using a 1.5 ml microfuge tube, clips, and a Velcro tape as shown in References (Disease models & mechanisms, 8(9), 1059-1069, 2015) to one hind leg of the mouse. All samples were dissolved in 0.5% carboxymethylcellulose (CMC) and orally administered once a day for 14 days from a day of application of leg fixation. After 2 weeks of leg fixation and oral administration of the sample, the gastrocnemius and the quadriceps of one hind leg were extracted, and the weights thereof were measured, normalized in proportion to the body weight, and then compared and shown in FIG. 1. As a result, compared to the normal group (Cont), the induction group (IM) induced muscle atrophy, resulting in a weight loss of about 40% in the gastrocnemius and about 33% in the quadriceps in proportion to the body weight. In the HMB-administered group (HMB 370), as the positive control group, the gastrocnemius decreased by about 24% and the quadriceps decreased by about 17%, showing about 16% and 16% of a muscle atrophy protective ability, respectively. On the other hand, in the low-dose group of *Aster spathulifolius* (AS 100), the gastrocnemius decreased by about 27% and the quadriceps decreased by about 22%. In the high-dose group of *Aster spathulifolius* (AS 200), the gastrocnemius decreased by about 25% and the quadriceps decreased by about 18%. Accordingly, the low-dose group of *Aster spathulifolius* (AS 100) exhibited a muscle atrophy protective ability of about 13% and 11%, respectively, and the high-dose group of *Aster spathulifolius* (AS 200) exhibited a muscle atrophy protective ability of about 15% and 15%, respectively. In other words, when considering the dose, it was confirmed that the *Aster spathulifolius* extract (100, 200 mg/kg) greatly alleviated the muscle weight lose due to leg fixation more than hydroxyl methylbutyrate (370 mg/kg) as the positive control group (HMB 370).

Example 3: Confirmation of Effect of Alleviating Reduction in Cross-Sectional Area of Muscle Fibers by Administration of *Aster spathulifolius* Extract Histological analysis was conducted to confirm whether an *Aster spathulifolius* extract improved the reduction in cross-sectional area of muscle fibers in a muscle atrophy mouse model. The gastrocnemius and quadriceps tissues extracted in Example 2 above were fixed with 4% paraformaldehyde and then subjected to hematoxylin and eosin staining (H&E staining), and thereafter, the cross-sectional area of the dyed muscle fibers was quantified through image J software, and the results were shown in FIGS. 2 and 3.

Figure 2:
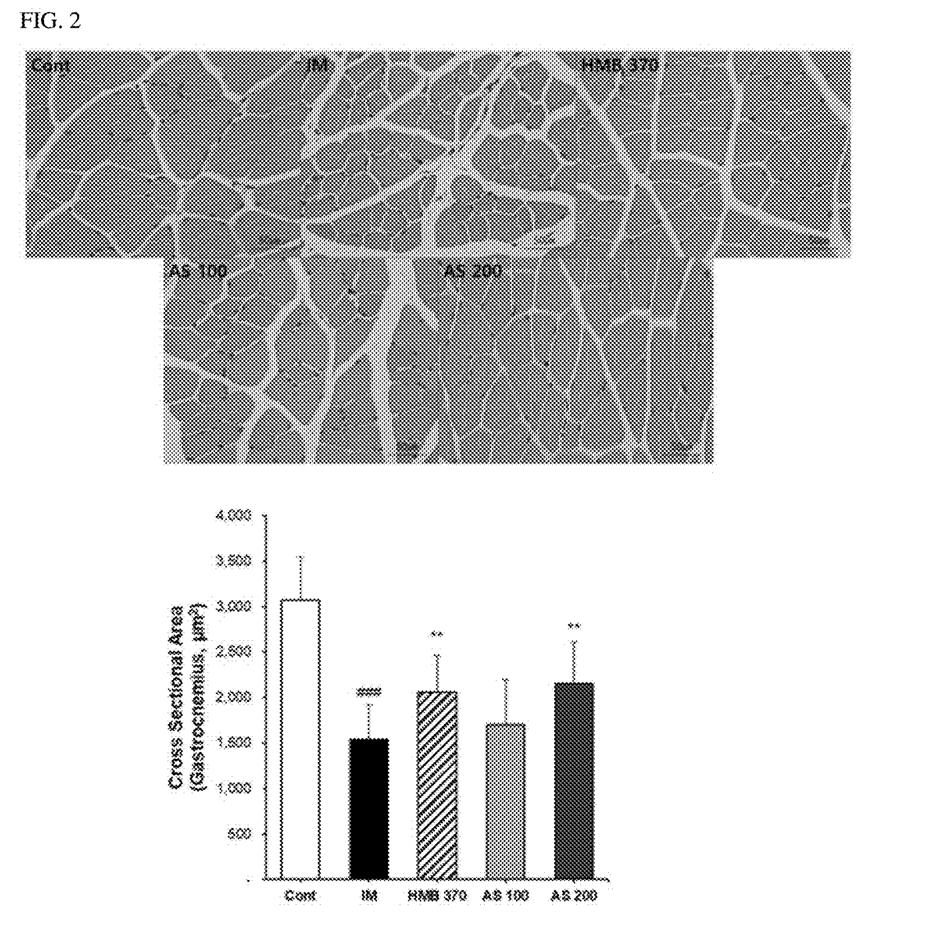
FIG. 2 illustrates a result of confirming an effect of alleviating the reduction in size of muscular fibers of an *Aster spathulifolius* extract, as a result of photographing H&E staining of the gastrocnemius and a result of measuring a cross-sectional area of the muscle fiber according to the administration of the *Aster spathulifolius* extract in the muscle atrophy mouse model.
Figure 3:
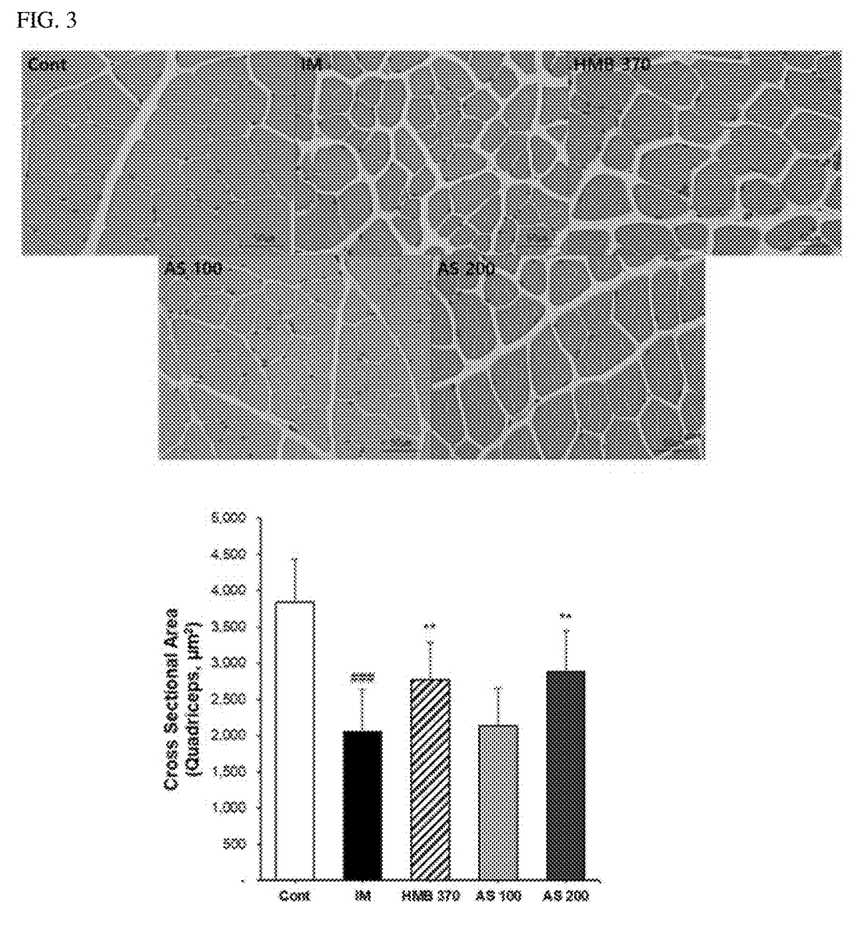
FIG. 3 illustrates a result of confirming an effect of alleviating the reduction in size of muscular fibers of an *Aster spathulifolius* extract, as a result of photographing H&E staining of the quadriceps and a result of measuring a cross-sectional area of the muscle fiber according to the administration of the *Aster spathulifolius* extract in the muscle atrophy mouse model.

As a result, in both muscle tissues, it was confirmed that compared to the normal group (Cont), in the induction group (IM), muscle atrophy was induced to greatly reduce the muscle fibers, and in the positive control group (HMB 370), and the low dose (AS 100) and the high dose (AS 200) of *Aster spathulifolius* extract, the reduction in muscle fiber size was alleviated.

As a result of the quantification of the cross-sectional area of each muscle fiber, in the gastrocnemius, as compared with the normal group (Cont), the induction group (IM) decreased by about 50%, and the positive control group (HMB 370), the low dose (AS 100) of *Aster spathulifolius*, and the high dose (AS 200) of *Aster spathulifolius* decreased by about 33%, 45%, and 30%, respectively. In the quadriceps, as compared with the normal group (Cont), the induction group (IM) decreased by about 47%, and the positive control group (HMB 370), the low dose (AS 100) of *Aster*

*spathulifolius*, and the high dose (AS 200) of *Aster spathulifolius* decreased by about 28%, 45%, and 25%, respectively.

In other words, in the gastrocnemius and the quadriceps, the protective ability against the cross-sectional area of muscle fibers was confirmed as 17% and 19% in the positive control group (HMB 370), 5% and 2% in the low dose (AS 100) of *Aster spathulifolius*, and 20% and 22% in the high dose (AS 200) of *Aster spathulifolius*, respectively. As a result, in the muscle atrophy mouse model, the *Aster spathulifolius* extract showed the protective ability against the dose-dependent reduction in the cross-sectional area of the muscle fibers, and when considering the dose, it was found to be more effective than HMB, the positive control group (HMB 370).

Example 4: Confirmation of Expression Regulation of Muscle Atrophy-Related Factors by Administration of *Aster spathulifolius* Extract To confirm whether the *Aster spathulifolius* extract improved the mRNA expression levels of muscle atrophy-related factors, muscle ring finger-1 (MuRF-1) and Atrogin-1, in a muscle atrophy mouse model, quantitative real-time PCR (qRT-PCR) was performed. The murf-1 and the atrogin-1 are representative muscle degradation-related factors that have been reported that the expression thereof is increased under a leg fixation condition with muscle specific E3 ubiquitin ligases. It has been known that the increase in murf-1 and atrogin-1 is associated with an increase in proteosome-dependent proteolysis to cause an increase in proteolysis, thereby contributing to muscle atrophy. The mRNA was extracted from the gastrocnemius extracted in Example 2 using RNA RED of Intron Co., Ltd. (Seongnam, Gyeonggi-do) according to the product instructions. The extracted mRNA was synthesized into cDNA using a cDNA synthesis kit from TaKaRa Co., Ltd. (Tokyo, Japan), and then qRT-PCR was performed using an ABI StepOnePlus™ Real-Time PCR System from Applied Biosystems Co., Ltd. (Foster City, USA).

Figure 4:
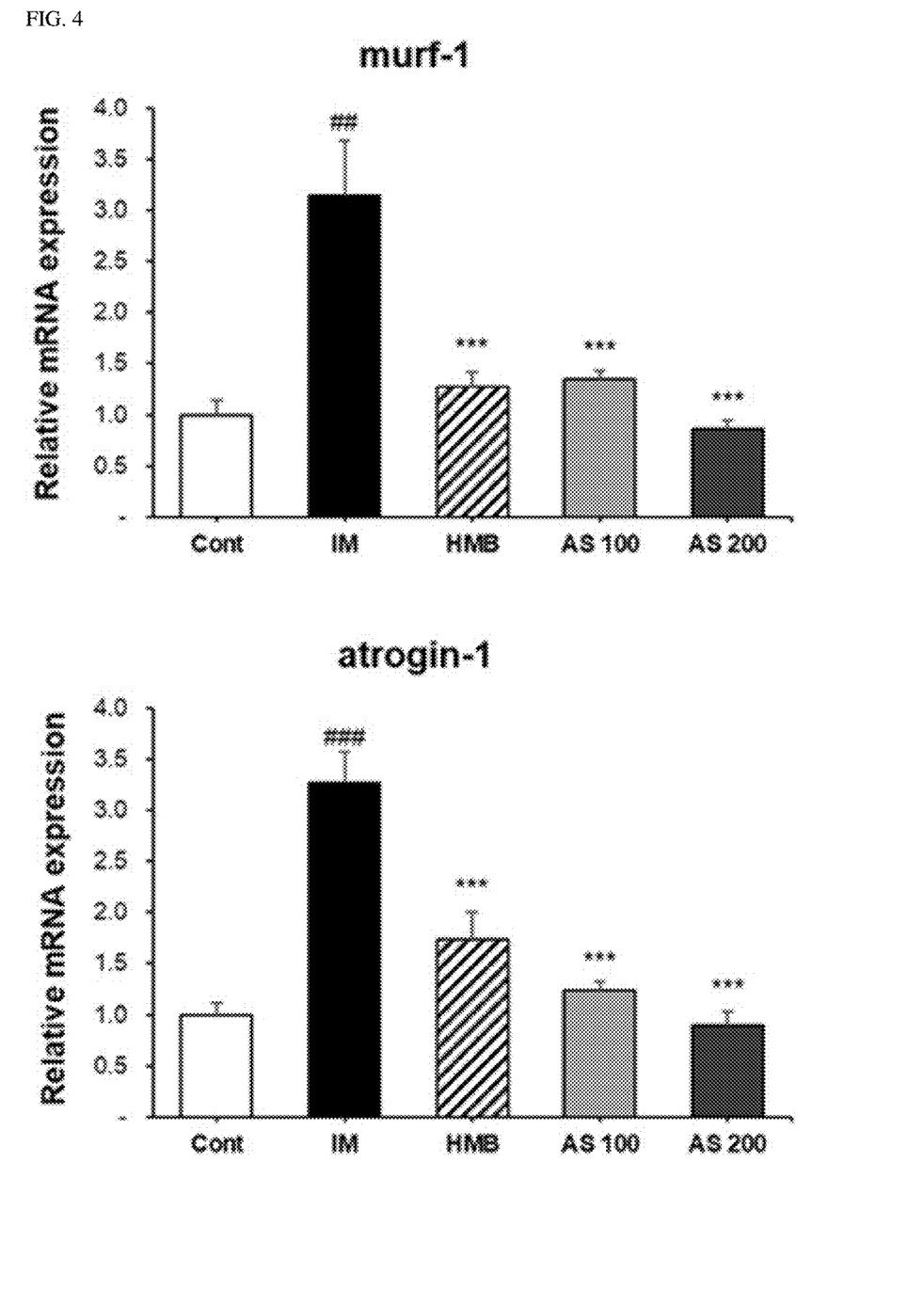
FIG. 4 illustrates a result of measuring changes in mRNA expression of muscle degradation-related factors in the muscle tissue according to the administration of the *Aster spathulifolius* extract in the muscle atrophy mouse model.

As a result, in the murf-1 gene expression results of FIG. 4, it was confirmed that the murf-1 gene expression was about 3 times higher in the induction group (IM) than the normal group (Cont). The positive control group (HMB 370), the low dose (AS 100) of *Aster spathulifolius*, and the high dose (AS 200) of *Aster spathulifolius* were confirmed to be about 1.7 times, 1.2 times, and 0.9 times, respectively. In addition, in the atrogin-1 gene expression results, it was confirmed that the atrogin-1 gene expression was about three times higher in the induction group (IM) than in the normal group (Cont). The positive control group (HMB 370), the low dose (AS 100) of *Aster spathulifolius*, and the high dose (AS 200) of *Aster spathulifolius* were confirmed to be about 1.3 times, 1.4 times, and 0.9 times, respectively.

As a result, in the muscle atrophy mouse model, it was confirmed that the *Aster spathulifolius* extract showed the protective ability against the increase in gene expression of concentration-dependent muscle degradation-related factors, and had better efficacy than the HMB, the positive control group (HMB 370).

Example 5: Confirmation of Expression Regulation of Muscle Atrophy- and Synthesis-Related Factors by Administration of *Aster spathulifolius* Extract In order to confirm whether the *Aster spathulifolius* extract improved the protein expression levels of MuRF-1 and Atrogin-1 as muscle atrophy-related factors, and Phosphorylated Mechanistic Target of Rapamycin (p-mTOR) as a muscle synthesis-related factor in a muscle atrophy mouse model, Western blot was performed. The mTOR is an important factor involved in regulation of protein translation initiation and is a representative factor involved in regulation of protein synthesis in muscle. The mTOR is a form in which the phosphorylated form (p-mTOR) is activated, and it is known that its expression is not changed significantly under continuous immobilization conditions, but when the activation is increased, muscle atrophy is alleviated. The mTOR contributes to an increase in muscle mass by inducing muscle protein synthesis by activating two factors that initiate mRNA translation, 4E-binding protein (4EBP1) and phosphorylated 70-kDa ribosomal S6 kinase (p70S6K) (The Korea Journal of Sports Science, 20(3): 1551-1561, 2011; The International Journal of Biochemistry and Cell Biology, 43(9): 1267-1276, 2011). Atrogin-1 and MuRF-1 are factors known to contribute to muscle atrophy by increasing protein degradation as mentioned in Example 4 above. The protein was extracted from the gastrocnemius extracted in Example 2 using a lysis buffer containing cOmplete™ protease inhibitor cocktail tablets from Roche Diagnostics Co., Ltd. (Indianapolis, USA). The extracted protein was adjusted to a constant protein concentration after checking the protein concentration according to the product instructions using a Pierce™ BCA Protein Assay kit from Thermo Fisher Scientific Co., Ltd. (Rockford, USA). The same amount of protein was subjected to electrophoresis in a 7.5% sodium dodecyl sulfate (SDS)-polyacrylamide gel, and then transferred to a polyvinylidine fluoride (PVDF) membrane using electroblotting. The membrane was blocked with 5% skim milk for 1 hour at room temperature and then incubated overnight with a primary antibody at 4° C. On the next day, the membrane was incubated with a horseradish peroxidase (HRP)-conjugated secondary antibody for 2 hours, and then developed using a LAS3000 luminescent image analyzer of Fujifilm Co., Ltd. (Japan, Tokyo). MuRF-1, Atrogin-1, and the secondary antibody were purchased from Santa Cruz Biotechnology Co., Ltd. (Santa Cruz, USA) and the p-mTOR antibody was purchased from Cell Signaling Technology Co., Ltd. (Danvers, USA).

Figure 5:
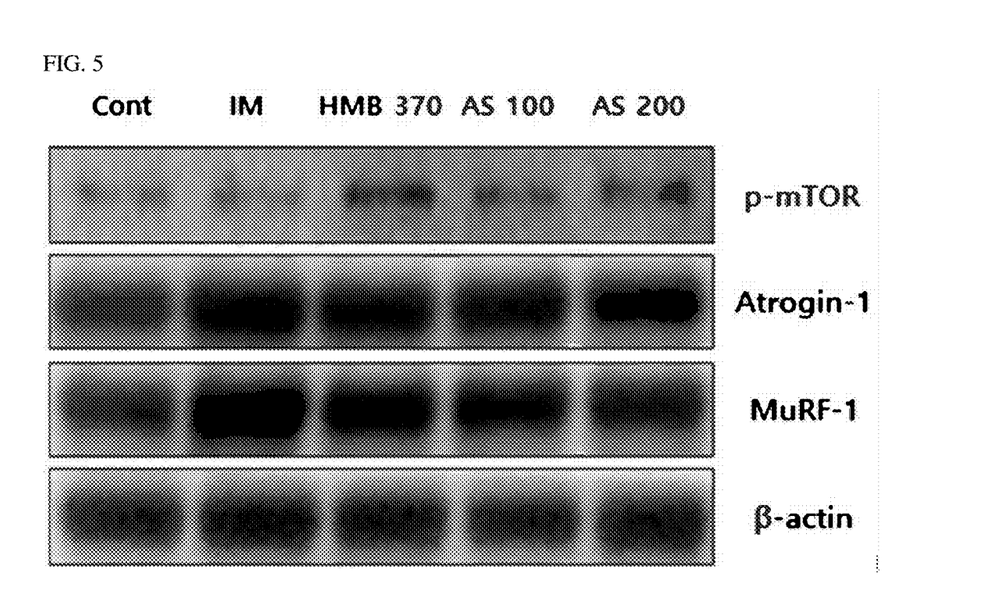
FIG. 5 illustrates a result of measuring changes in expression of muscle degradation-related factors and muscle synthesis-related factors in the muscle tissue according to the administration of the *Aster spathulifolius* extract in the muscle atrophy mouse model.

In the p-mTOR protein expression results of FIG. 5, there was no significant difference between the normal group (Cont) and the induction group (IM), but the p-mTOR protein expression showed a large increase in the positive control group (HMB 370) and showed a dose-dependent increase even in the *Aster spathulifolius* extract administration groups (AS 100 and AS 200). In the results of Atrogin-1 and MuRF-1 protein expression, it was confirmed that the expression thereof was significantly increased in the induction group (IM) compared to the normal group (Cont). The *Aster spathulifolius* extract showed a dose-dependent decrease, and the positive control group (HMB 370) showed a similar level of expression to the low dose of *Aster spathulifolius* extract (AS 100).

As a result, in the muscle atrophy mouse model, the *Aster spathulifolius* extract showed a protective ability against changes in protein expression of concentration-dependent muscle regeneration and degradation-related factors, and showed better efficacy in reducing the increase of muscle degradation-related factors.

The aforementioned description of the present invention is to be exemplified, and it can be understood by those skilled in the art that the technical spirit or required features of the present invention can be easily modified in other detailed forms without changing. Therefore, it should be appreciated that the aforementioned exemplary embodiments described above are all illustrative in all aspects and are not restricted.

INDUSTRIAL APPLICABILITY

As described above, the *Aster spathulifolius* extract according to the present invention has effects of not only inhibiting the expression of muscle degradation-related factors and increasing the expression of muscle synthesis-related factors, but also alleviating the reduction in a muscle tissue weight and a cross-sectional area of muscle fibers. Therefore, the *Aster spathulifolius* extract of the present invention can be not only usefully used in the prevention, improvement or treatment of muscle diseases including muscular dystrophy, but also usefully used as a composition for improving muscle functions.

What is claimed is:

1. A method for treating or improving muscular diseases in a subject in need thereof, the method comprising administering an effective amount of a composition comprising an *Aster spathulifolius* extract as an active ingredient to the subject in need thereof, wherein the extract is an extract extracted by alcohol having 1 to 6 carbon atoms, or a mixture of water and alcohol having 1 to 6 carbon atoms.

2. The method of claim 1, wherein the composition is a pharmaceutical composition, or a food composition.

3. The method of claim 1, wherein the muscular disease is at least one selected from the group consisting of atony, muscular atrophy, muscular dystrophy, muscle degeneration, myotonia, muscular dystrophy, amyotrophic lateral sclerosis, myasthenia, cachexia, and sarcopenia.

4. The method of claim 1, wherein the subject is a livestock selected from the group consisting of cows, pigs, chickens, ducks, goats, sheep and horses.

* * * * *